(12) United States Patent
Savic

(10) Patent No.: US 7,479,115 B2
(45) Date of Patent: Jan. 20, 2009

(54) COMPUTER AIDED DIAGNOSIS OF LUNG DISEASE

(75) Inventor: Michael Savic, Bradenton, FL (US)

(73) Assignee: Savic Research, LLC, Bradenton, FL (US)

(*) Notice: Subject to any disclaimer, the term of this patent is extended or adjusted under 35 U.S.C. 154(b) by 274 days.

(21) Appl. No.: 11/467,350

(22) Filed: Aug. 25, 2006

(65) Prior Publication Data
US 2008/0082017 A1  Apr. 3, 2008

(51) Int. Cl.
A61B 5/00  (2006.01)
(52) U.S. Cl. .................. 600/529; 600/586
(58) Field of Classification Search .......... None
See application file for complete search history.

(56) References Cited

U.S. PATENT DOCUMENTS 5,036,857 A * 8/1991 Semmlow et al. ......... 600/528
5,327,893 A * 7/1994 Savic ..................... 600/454
2007/0191740 A1* 8/2007 Shertukde et al. ........ 600/586

* cited by examiner

Primary Examiner—Robert L Nasser
(74) Attorney, Agent, or Firm—Notaro & Michalos P.C.

(57) ABSTRACT

A method and apparatus by which lung deceases are identified uses computer analysis of sound signals that are picked up from various locations on the chest walls of a subject by a modified stethoscope. The modification includes a small microphone in one of the hoses of the stethoscope. Signals from the microphone are input to a computer such as a personal computer or PC for processing. The computer extracts from these signals features which are dominant for particular lung diseases. A classifier classifies these features, determines if the lungs are diseased, and identifies the disease.

28 Claims, 4 Drawing Sheets

COMPUTER AIDED DIAGNOSIS OF LUNG DISEASE

FIELD AND BACKGROUND OF THE INVENTION

The present invention relates generally to the field of medical equipment for the diagnosis of ailments, and in particular to a new and useful apparatus and method for helping with the diagnosis of lung diseases.

The Signal and Speech Research Group (SRG) of Rensselaer Polytechnic Institute (RPI) has carried out research on algorithms for signal processing and their application since 1981. The group has been led by Professor Michael Savic, the inventor of the present application. Since 1985 the SRG has focused on high-risk, innovative research in all aspects of signal processing. Current areas include speaker recognition, language identification, detection of cholesterol deposits in blood vessels, speech recognition, automatic pipeline leak detection, voice character transformation, speaker separation (the cocktail party problem) and others.

Patents have been awarded for some of this work to RPI and Professor Savic, including: U.S. Pat. No. 7,024,360 for System for reconstruction of symbols in a sequence; U.S. Pat. No. 5,675,506 for Detection of leaks in vessels; U.S. Pat. No. 5,623,421 for Monitoring pressurized vessels for leaks, ruptures or hard hits; U.S. Pat. No. 5,416,724 for Detection of leaks in pipelines; and U.S. Pat. No. 5,327,893 for Detection of cholesterol deposits in arteries. These patents are all incorporated here by reference.

Chest auscultation, that is, the act of listening for sounds made by the lungs to aid in the diagnosis of certain disorders, is an effective, nonintrusive and inexpensive way to assess the condition of a patient's lungs. Many clinicians use chest auscultation in a cursory manner because they are not skilled in recognizing certain lung sounds.

A brief explanation of this technique can be found in an article at URL: http://www.leedsth.nhs.uk/sites/emibank/clinicians/nursing/documents/auscul ta.pdf, entitled "Chest Auscultation," by Bob McMaster, February/2001.

The training of doctors for this technique is long and difficult. Moreover, the human ear is sensitive to a certain sound frequency range only (e.g. 15 to 20,000 Hz) and some significant lung sounds are not in this range and therefore will not be heard, even by the most highly trained practitioner.

To better understand the present invention, a brief description of breath sounds and of what is under investigation is necessary. Many distinctive sounds are generated by a diseased lung. These may be roughly grouped into two broad categories, the adventitious sounds and the abnormally transmitted sounds. See, for example, Lehrer, S., "Understanding Lung Sounds", W.B. Saunders Company, 1993. Sounds like crackles, wheezes and pleural friction rubs are included in the adventitious sounds group while sounds like egophony, pectoriloque, bronchophony, bronchial breathing and abnormally diminished breath sounds are included in the abnormally transmitted sounds group. Recent scientific investigations, aided by advances in acoustics and electronics, provide insights into the mechanism of production of these sounds.

Diseases that are explored here are identifiable in the adventitious breath sounds and especially in crackles. Crackles are short, explosive, nonmusical sounds that can be described as to quantity (scanty or profuse) and timing (inspiratory or expiratory, early or late). Two commonly accepted theories suggest that crackles can be produced by the bubbling of air through airway secretions or by sudden opening of small airways (see: Wilkins, L. R. at al, "Lung Sounds: A practical guide", Mosby-Yaer Book, Inc., 1996). Crackles associated with the movement of airways secretions in larger airways are typically coarse and may occur during both inspiration and expiration. They may clear with suctioning of effective coughing. Crackles associated with the sudden opening of airways may be produced by a rapid equalization of pressure between open and collapsed airways (see: Ploysongsang, Y. and Schondeld S. A., "Mechanism of production of crackles after atelactasis during low-volume breathing", Am Rev Resp Dis 126:413, 1982; and Forgacs, P., "The functional basis of pulmonary sounds", Chest 73:399, 1978). These crackles are inspiratory sounds, which may occur when peripheral airways pop open as atelactatic regions are inflated.

With atelactasis due to shallow breathing, the crackles often disappear after a few deep breaths or after changes in the position; whereas with pulmonary fibrosis, the crackles persist. In mild pulmonary fibrosis, a disease that is explored here, the crackles are predominantly heard late in inspiration, but may become pan-inspiratory with an end-inspiratory accentuation as the disease progresses. Late-inspiratory crackles are often repetitive with several respiratory cycles and initially identified in dependent lung zones. Late-inspiratory crackles indicate a loss in lung volume and are audible over the chest walls. Early-inspiratory crackles are scanty, low-pitched and audible at the mouth as well as over the chest.

Although the present invention to be disclosed here can be used to identify any lung disease that produces sounds that can be processed using the apparatus and method of the invention, two particular diseases have been used to demonstrate the effectiveness of the invention and, therefore are discussed in some detail here.

Chronic Bronchitis

This condition produces excessive secretion of mucus, resulting in chronic cough productive of sputum. Pathologically, bronchitis is characterized by proliferation and hyperplasia of the mucus glands in the large airways, extending abnormally into small airways, often without evidence of inflammatory changes, although the changes may be associated with bacterial infection. Chronic bronchitis is commonly caused by the inhalation of cigarette smoke, although the disease is found in a few nonsmokers as well, particularly miners and people living in polluted urban environments. The principal complication associated with chronic bronchitis is the development of obstructive airway disease.

Interstitial Fibrosis

This condition, also called interstitial pneumonitis, is associated with interstitial and alveolar infiltrates and fibrosis. Patients complain of coughing, or difficulty in breathing and, although rarely, of fever. Pulmonary function studies show restriction and are sensitive indicators of the extend of the illness. Interstitial fibrosis may be caused by cancer chemotherapeutic agents (bleomycin, cyclophosphamide, methotrexate), radiation therapy, the antibiotic nitrofurantoine, high oxygen concentrations inhaled over a long period, and heavy metals such as gold. It is most often idiopathic.

SUMMARY OF THE INVENTION

It is an object of the present invention to provide an apparatus and a method or technique by which lung deceases can be detected and categorized without relying on human hearing and interpretation of what was heard. Using features of sound signals from the chest of a patient and applying digital signal processing, a classifier determines if the lungs are healthy or not, and, if not, the classifier identifies the lung disease. While the apparatus and method of the invention can be used to detect any lung decease, the invention is demonstrated in this disclosure by the detection of chronic bronchitis and fibrosis.

Another object of the invention is to use autoregressive modeling for recognition and identification of lung diseases. Autoregressive modeling provides suitable tools for recognition and identification of particular lung diseases.

A still further object of the invention is to use preferably LPC and/or PARCOR coefficients.

Another object of the invention is to provide an apparatus for identifying a lung disease in a subject, the lung disease producing lung sounds that are characteristic of the lung disease, the apparatus comprising: a stethoscope for acquiring the lung sounds from the subject; a transducer operatively connected to the stethoscope for converting the lung sounds to an electric signal; and a computer-based analyzer for analyzing the signal, to identify the lung disease.

The stethoscope may include at least one hose for conveying the sounds, and the transducer may be a microphone inserted into the hose or connected to the hose for picking up sounds in the hose.

The computer-based analyzer may comprise a computer that is programmed for extracting and classifying features from lung sounds using autoregressive modeling. Based on the signal features characteristic for a particular disease, the software classifier identifies the lung disease.

It is noted that the data base used to train and test the system of the present invention included recordings of the chest sounds caused by 53 lung diseases. These recordings were made professionally at prominent hospitals and where originally meant for use in teaching and tutoring medial personnel in the technique and, to some extent, art of chest auscultation.

Accordingly, another object of the invention is to provide an apparatus and a method which mechanizes, standardizes and improves the diagnostic results that can be achieved with chest auscultation.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
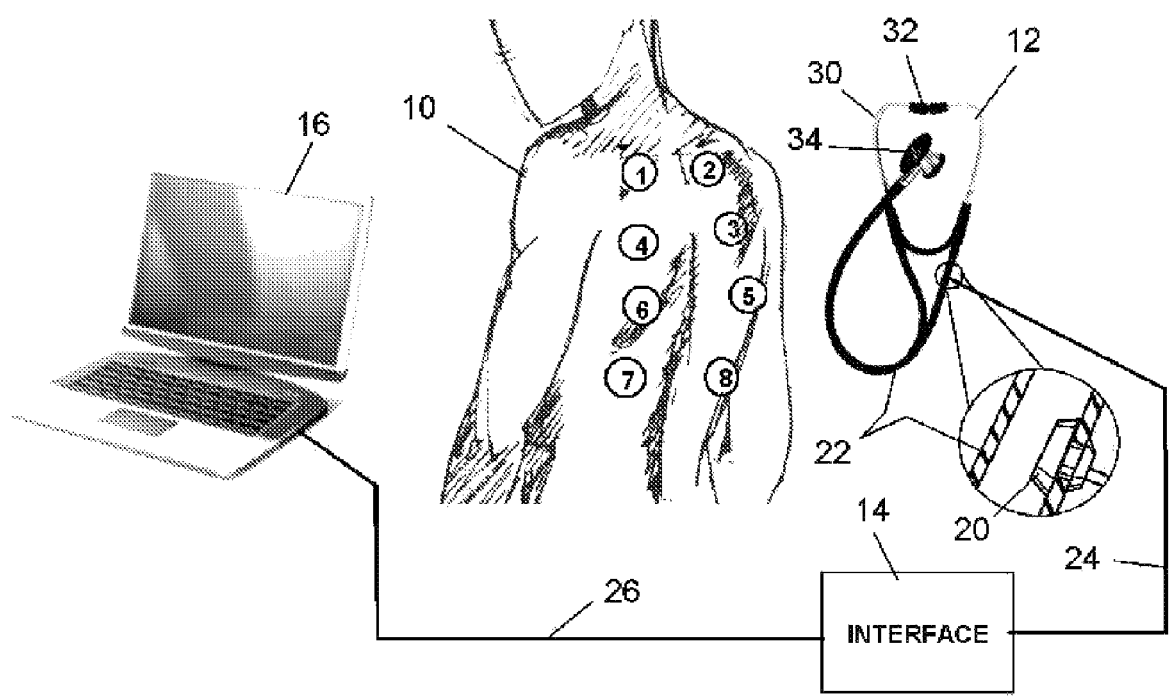
FIG. 1 is a schematic representation of the apparatus of the present invention.

Referring now to the drawings, FIG. 1 shows how lung sounds or signals are picked up from various locations, e.g. points ①to ⑧ on the front or back of the chest of a patient 10, by a modified stethoscope 12, and are input, either directly, or through an interface 14, to a computer 16. These points can be of the known types that follow the current conventions for chest auscultation, or may be newly discovered points where perhaps higher or lower frequency sounds that are outside the human hearing range have been discovered to be associated with lung diseases by use of the present invention in the future.

According to the present invention, a small microphone or other sound transducer 20, that is sensitive and capable of picking up sounds in a wide frequency range and converting them to electrical audio signals, is installed in one of the hoses 22 of the stethoscope 12. The transducer 20 is connected by a cable 24 to the interface 14, or can be wirelessly connected to the interface, for receiving the audio signals. A further cable 26 or a wireless connection, connects the interface to the computer 16. Alternatively the interface may be incorporated into the computer. In any case, a computer-based analyzer is provided for analyzing the signal to identify the lung disease.

After a series of preliminary procedures in the interface 14, these signals are converted into a suitable form for computer processing in computer 16 which has been programmed with the signal analyzing algorithms needed according of the present invention. This includes analog-to-digital conversion, filtering and frequency downsampling. Next, features are extracted using autoregressive methods. Feature extraction means obtaining parameters which distinguish one class from another, in this case, classes are particular lung diseases.

A classifier is used to recognize if the lungs are diseased, and if they are, to identify the disease. Many different classifiers can be used for this purpose, however the system was exemplified using two classifiers, a simple two dimensional Graphical Classifier (GC) and a more sophisticated, Artificial Neural Net (NN) classifier.

Other suitable and known classifiers, or classifiers that might be later discovered by those skilled in the art, could be used as well. It is important to mention that samples used in this research are real lung sounds, recorded from real patients and not artificially generated sounds.

Summary of the Approach

Computer analysis of lung sounds starts with processing of the signal data input to the computer 16, which is created from the signals from the stethoscope mounted transducer 20.

Processing includes, feature extraction using autoregressive methods, dominant feature selection, initialization, and training the neural network with sounds characteristic for particular diseases.

Preparation of the data samples is performed using various software packages for processing of sound. Feature extraction is accomplished using MATLAB routines. The neural network of the invention was constructed and trained using the Neural Network toolbox of MATLAB. MATLAB is a high-level language and interactive environment that enables one to perform computationally intensive tasks.

Further Description of the Modified Stethoscope

A standard stethoscope 12, has two hoses 20 that connect to parts 30 that end in ear-pieces 32 to be inserted into a physician's ears. The hoses 20, either together or after they are merged into a single hose, connect to the bell or sound pick-up 34 that is placed on the chest of the patient. The small microphone or transducer 20 is inserted into one of the hoses of the stethoscope as noted above. During examination, the stethoscope is placed on the chest of the patient using known chest auscultation techniques to pick up sounds from the lungs. The output signal from the microphone is sent to the computer 16.

Some lung diseases can be easier identified from the sound during the inspiration period, and some others during the expiration. For example, in the case of bronchitis the inspiratory period is essential. In this case the invention is used to collect the information contained in the signal only during the period when the patient inhales. A simple way to record the sound during the inspiration (inhaling) period is to ask the patient to inhale and hold his or her breath. A similar procedure is used if the sound during the expiration (exhaling) should be investigated. The inhaling and exhaling cycles can be separated automatically using an algorithm like the Hidden Markov Model as in the procedure described in U.S. Pat. No. 7,024,360 which is incorporated here by reference.

After preliminary processing, the signal from the microphone is converted into suitable form for computer processing. Preliminary processing includes analog-to-digital conversion, filtering, and frequency downsampling. Next, multiple features from signals are extracted. These features can be LPC (Linear Predictive Coding) Parameters, Fourier Coefficients, PARCOR (Partial Autocorrelation) Coefficients, Cepstrum Coefficients, Autocorrelation Coefficients, or others.

Equations for extraction of these features are well known and are given in the literature, such as in the articles:

Oppenheim V. A., Schafer, W. R., "Discrete Signal Processing", Prentice Hall, 1999;

Iyer, V. K, Ramamoorthy, P. A., and Ploysongsang, Y., "Autoregressive modeling of lung sounds: characterization of source and transmission", IEEE Trans. Biomed. Eng. BME-36(11), 1133-1137, 1989;

Makhoul, J., "Linear prediction: a tutorial review", Proc. IEEE 63:561-580, 1975;

Kay, S. M., "Recursive maximum likelihood estimation of autoregressive processes", IEEE Trans. Accoust. Speech Signal Processing ASSP-28:292-303, 1980; and Orfanidis, S., "Optimum Signal Processing", MacMillan, New York, 1985.

Some features are more suitable to identify particular diseases than other features. Autoregressive Coefficients have been found by the inventor to be very good features, because they discriminate particular diseases better than other features. "Good features" or "dominant features" for a particular disease are features that require the least amount of computation to accurately identify a particular disease. For best results "good features" should be used. Features must be selected very carefully from a variety of available features using some kind of "Discriminant Analysis." Dominant Feature Selection means the selection of those features which best distinguish one disease from another.

Data Processing

The procedure for detection and categorization of lung diseases according to this invention is performed in two phases; Training and Recognition.

Training (Feature Extraction and Selection)

A number of features are extracted from a data base of lung sounds (signals) characteristic for different lung diseases. These sounds are here called "Training Signals" and are used to train the computer to recognize particular lung diseases. "Training Signals" are available on tapes or CDs, and recordings of these lung sounds were made professionally at prominent hospitals, and are used for teaching and tutoring medical personnel as noted.

The method of the invention is exemplified using LPC and PARCOR coefficients as features. Other features can be used as well, such as the Fourier Coefficients, Cepstrum Coefficients, Autocorrelation Coefficients, or others, however LPC and PARCOR Coefficients turned out to be suitable for signals from the lungs, and they provided good results.

The best features from among the extracted features are then selected. The best features or the dominant features for a particular disease are features that best distinguish one disease from another, using minimum computer power. Dominant features for particular diseases are extracted from the Training Signals, and are stored in the memory of the computer to create a data base of dominant features for particular diseases.

Recognition

During this phase, sound signals are picked up from the chest of the patient 10 using the modified stethoscope 12, and then brought into the computer 16 after preliminary processing in interface 14, or inside the computer if the preliminary processing functions are included in the computer itself.

In either case, the audio signals from the microphone 20 are converted into suitable form for computer processing. Preliminary processing includes analog-to-digital conversion, filtering, and frequency downsampling. Next, multiple features from the signals are extracted. These features can be LPC coefficients, Fourier Coefficients, PARCOR Coefficients, Cepstrum Coefficients, Autocorrelation Coefficients, or others as with the training phase.

The method of the invention is here exemplified using LPC and PARCOR coefficients as features. These features produced good results, however other suitable features can be used as well. Next, the extracted features are forwarded to the classifier.

The classifier is a device or program running in the computer that makes the decision based on the extracted features. The "classifier" determines if the lungs are healthy or diseased, and identifies the disease. Many classifiers can be used to make these decisions, however in a preferred embodiment of the invention two classifiers have been selected and implemented. These two classifiers are the two dimensional Graphical Approach (GA), and the Neural Net (NN) classifier.

These classifiers were used to identify if the lungs are healthy or diseased, and if the lungs are unhealthy, to identify the decease.

Reasons for Implementing Autoregressive Modeling

Sound signals from the lungs have some specific properties: Parameters of these signals are degraded due to background noise. The length of these signals is usually short, for instance the length of the inspiration cycle is about 0.8 seconds. If the signal-to-noise ratio is small, traditional analysis methods like the Fourier transform, fail to provide an accurate spectrum. In this situation FFT (Fast Fourier Transform) provides poor frequency resolution, and it may produce even false spectral responses. To avoid these problems, the method that is used in this invention is the autoregressive parametric model analysis. Autoregressive modeling has been found to exhibit outstanding performance when the signal has sharp peaks. Parametric model analysis involves the selection of a suitable model, and the estimation of parameters of that model.

The assumption is made that lung sounds picked up from the chest of the patient are produced by an all-pole filter. This is justified because sounds from the lungs have indeed such properties that they can be represented by an Autoregressive Parametric Model. Consequently the autoregressive model was used in this invention.

Pattern Recognition—General

People recognize faces of friends in a crowd, voices of acquaintances, favorite musical compositions, and the like. In order to do this, light or sound waves emitted from objects are recognized by our senses and we use our capable of identifying and discriminating such objects. This process is called pattern recognition. In more scientific terms, the determination that an object from a general population P belongs to a known subpopulation S is called pattern recognition. In our case P are all sound signals from the chest of the patient, and S is the sound signal for a particular lung disease. The subpopulation S is called the class, and it is defined by particular features that accurately describe this subpopulation, these features are, for the present invention the Autoregressive Coefficients, e.g. the LPC and PARCOR coefficients.

The input to a pattern recognition system is a set of N attributes, in the present case features from sounds from the chest, and the output are the classified features.

Usually, the input is represented like an N-dimensional vector $x=[x_1, x_2, x_3, \ldots, x_n]$, the pattern vector and is introduced to the system after it is transformed to a reduced set of features, the feature vector $f=[f_1, f_2, f_3, \ldots, f_n]$, where m<n. The pattern vectors are obtained after measurements. In the present case, the measurement of the amplitude of the breathing sounds versus time. The total of the pattern vectors form the pattern space while the total of the feature vectors form the vector space. The system can recognize an object S comparing its feature vector with the feature vector of a known class $c=[c_1, c_2, c_3, \ldots, c_m]$ according to a threshold value which is the difference between the feature vector and the class.

Pattern recognition is performed in two steps, feature extraction and classification, i.e. input signal→feature extraction→classification.

Features

An object in a population is characterized by different attributes, many of them can be used to separate or distinguish this object among similar or different ones. There are attributes that can distinguish objects and there are attributes that cannot distinguish objects. For instance, color is a good attribute to distinguish oranges from apples but it cannot distinguish lemons from grapefruits. The attributes are called features in pattern recognition terminology and they are extracted by the use of linear or non-linear transformations.

More particularly, let s be an N-dimensional pattern vector, $s=[s_1, s_2, s_3, \ldots, s_n]$. The transformation $f=L\{s\}$ is a linear or a non-linear transformation that maps the s vector into an f vector, the feature vector, where m<n. It should be noticed that since m<n, this mapping is not one-to-one, and the inverse transformation $f=L^{-1}\{s\}$ is not unique. Feature extraction is a process that essentially reduces the dimensionality of the pattern vector N to the dimensionality of the feature vector M. This process is useful for the following reasons. The feature space is often physically more meaningful than the pattern space. For example, in speech analysis, the frequency spectrum is more meaningful than the speech waveform. If a Fourier transform of a signal is taken the frequency components could be better features for classification than the features in the time domain. During the transformation from the time domain into the feature space it is important to retain as much information from the pattern vector as possible, in a more efficient way. This is achieved by an appropriate selection of the set of features that contain all the information of the pattern vector required for classification, but in lower dimensional vectors. In addition, there may be some prior knowledge that the measurements are redundant, and that the data are highly correlated. If this is the case, the dimensionality can be reduced with very little loss of information.

Furthermore, the redundant information can introduce noise and degrade system performance. Any set of extracted features that contains all necessary information but is not redundant, is called an optimal feature set In practice, near-optimal sets are desirable. Consequently, an important step in the classification process is the selection of a suitable set of features. As mentioned before, there are features that distinguish one class (disease) but cannot distinguish another class (disease). The selection of the features is therefore, highly dependent on the nature of the objects. It is proven that highly correlated features increase the classification error, while uncorrelated (independent) features provide better discrimination. Features can be characterized as correlated when features of one object depend strongly on the features of another object. A measure of dependency is, therefore, desired. The most common measure of dependency is the correlation coefficient.

Let the feature vectors X have the dimension N and let the components of the feature vector $x=[x_1, x_2, x_3, \ldots, x_n]$, be ordered according to the ranked feature importance. This importance may be assigned by the total magnitude of its range (the greatest values minus the least values) or its variance. If $\{x^1, x^2, \ldots x^r\}$ is a sample of feature vectors that are numerous and different, so as to be from all of the various classes, then the sample correlation between the features is defined according to the article: Iyer, V. K, Ramamoorthy, P. A., and Ploysongsang, Y., "Autoregressive modeling of lung sounds: characterization of source and transmission", IEEE Trans. Biomed. Eng. BME-36(11), 1133-1137, 1989; as a function of the expected value of the i-th component over the sample population T and the expected value operator. A standardized dimensionless correlation coefficient can also be found and expression correlation coefficients can be compared for different situations.

Correlation coefficient of any feature X with itself is 1. Two features are independent if the correlation coefficient approaches zero. Uncorrelated features would produce a graph of multiple clusters of point that are spaced far from each other while a case where features are highly correlated would look more like FIGS. 2 to 5, which will be discussed later in this disclosure.

Except in a very few special cases, the optimal selection can only be done by testing all possible sets of M features chosen from the N data objects (Trasos Axiotis, RPI, Master's Project. 2000). Of course, the number of different combinations may be a very large number. Thorough search is the only way to find a true optimal feature set, but this is not practical in most situations (Iyer, V. K, Ramamoorthy, P. A., and Ploysongsang, Y., "Autoregressive modeling of lung sounds: characterization of source and transmission", IEEE Trans. Biomed. Eng. BME-36(11), 1133-1137, 1989).

It should be mentioned that the measurement selection is a very important process and the success or failure of pattern recognition strongly depends on the selection of which measurements to make and how these measurements are performed. For instance, a low quality measurement can introduce a large amount of noise causing the extracted feature vector to diverge significantly from what it really is.

The GA (Graphical Approach) Classifier

In order to have some idea about the quality and usefulness of the extracted features, and to visualize same properties of the extracted features, it is practical to use the first two coefficients of these features and to represent them in a two dimensional representation, i.e. in a plane.

Figure 2:
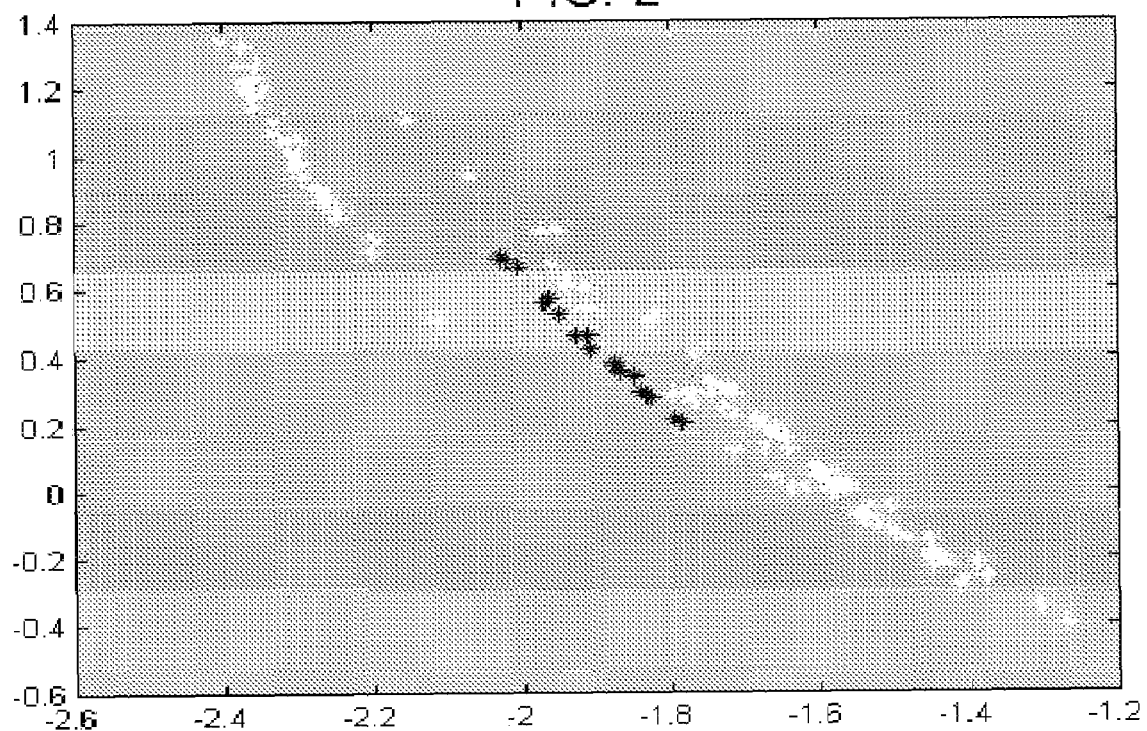
FIG. 2 is a two-dimensional (2-D) representation of LPC coefficients 2 and 3 produced according to the present invention where the dark stars are indicative of samples from patients with bronchitis and the other stars are from other samples.
Figure 3:
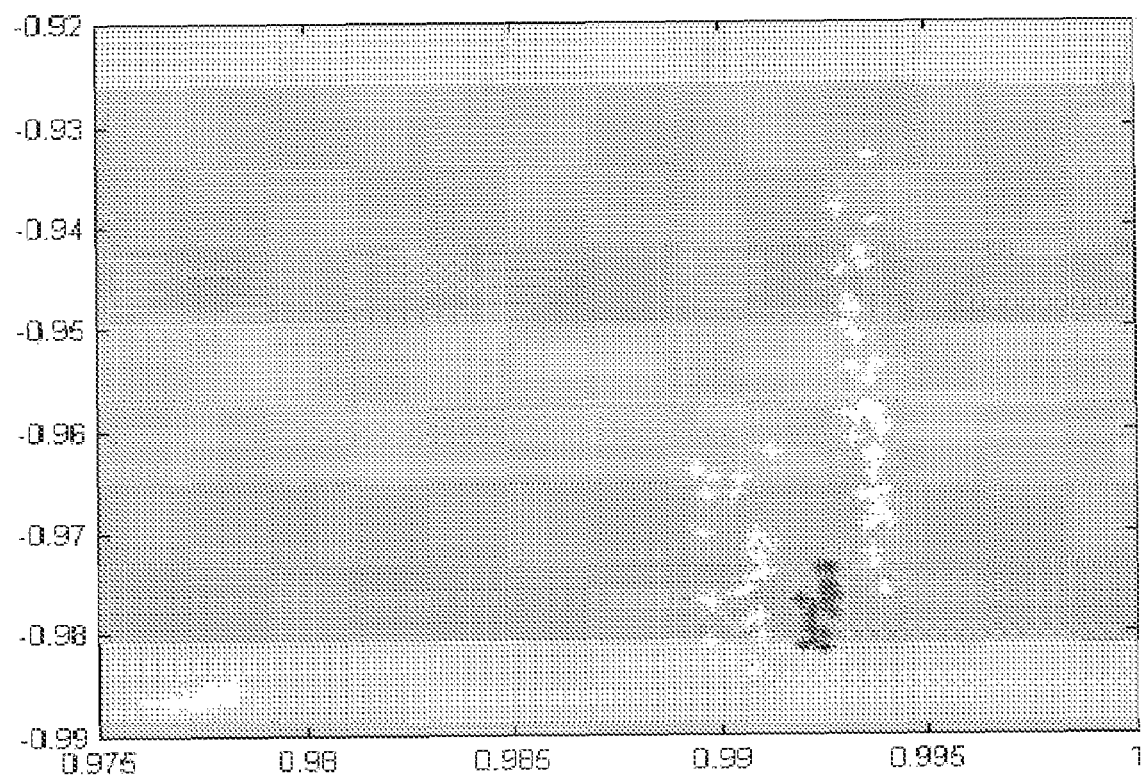
FIG. 3 is a two-dimensional (2-D) representation of PARCOR coefficients 2 and 3 produced according to the present invention, where the dark stars are indicative of samples from patients with bronchitis and the other stars are from other samples.
Figure 4:
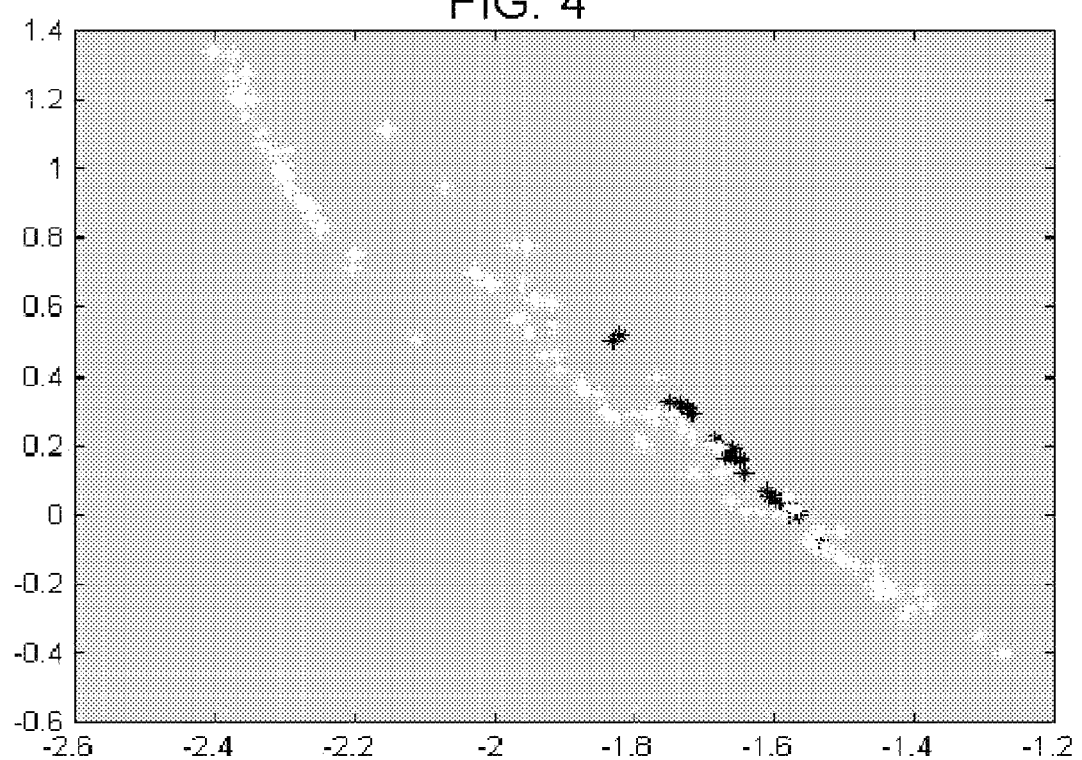
FIG. 4 is a two-dimensional (2-D) representation of LPC coefficients 2 and 3 produced according to the present invention where the dark stars are indicative of samples from patients with fibrosis and the other stars are from other samples.
Figure 5:
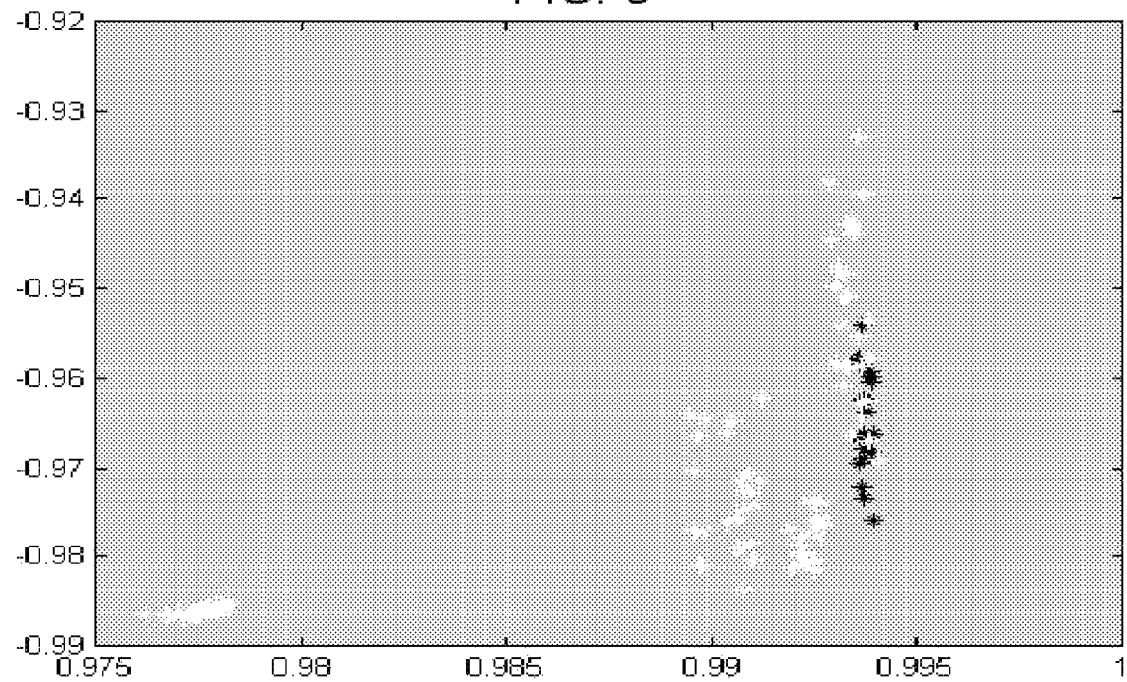
FIG. 5 is a two-dimensional (2-D) representation of PARCOR coefficients 2 and 3 produced according to the present invention where the dark stars are indicative of samples from patients with fibrosis and the other stars are from other samples.

For example the first two LPC coefficients $LPC_1$ and $LPC_2$ can be extracted for each sample, and plotted in two dimensions as shown in FIGS. 2 and 4.

This classifier classifies features in two dimensions, it is simple and it gives good results if the features and the two dimensions are selected so that clusters do not overlap. If the Neural Net (NN) classifier to be explained later, is used, the selection of features and dimensions is not as critical as in the GA classifier, because the Neural Net performs multidimensional classification.

The mathematical function that estimates the LPC coefficients normalizes the output by dividing every coefficient by the first one. The first coefficient is therefore always 1 (one) and is ignored because it does not carry any information. Therefore, only the higher coefficients are used in this approach. Consequently, in the presented examples only the second and third coefficients are used. Since the PARCOR (Partial Correlation Coefficients) are dependent on the LPC coefficients, only the second and the third PARCOR coefficient are used in the shown examples. Mathematical algorithms can be used to extract various features from the signal that is picked up from the chest of the patient, however a simple and practical way to extract these features is to use the prepackaged software routines from the MATLAB "Signal Processing Package". As mentioned, in order to provide some visualization, the location of a number of sampling datapoints for various diseases is presented in two dimensions. The two dimensional diagrams are generated and plotted using the MATLAB routines: cbr2d and cfb2d.

Figure 6:
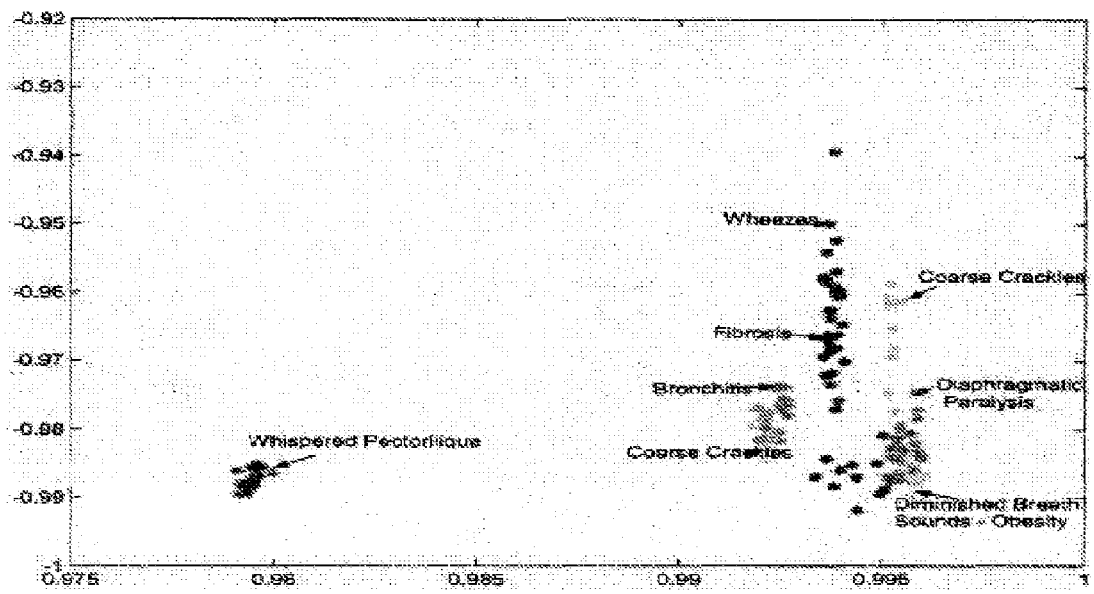
FIG. 6 is a two-dimensional (2-D) representation of various diseases using PARCOR coefficients 2 and 3.
Figure 7:
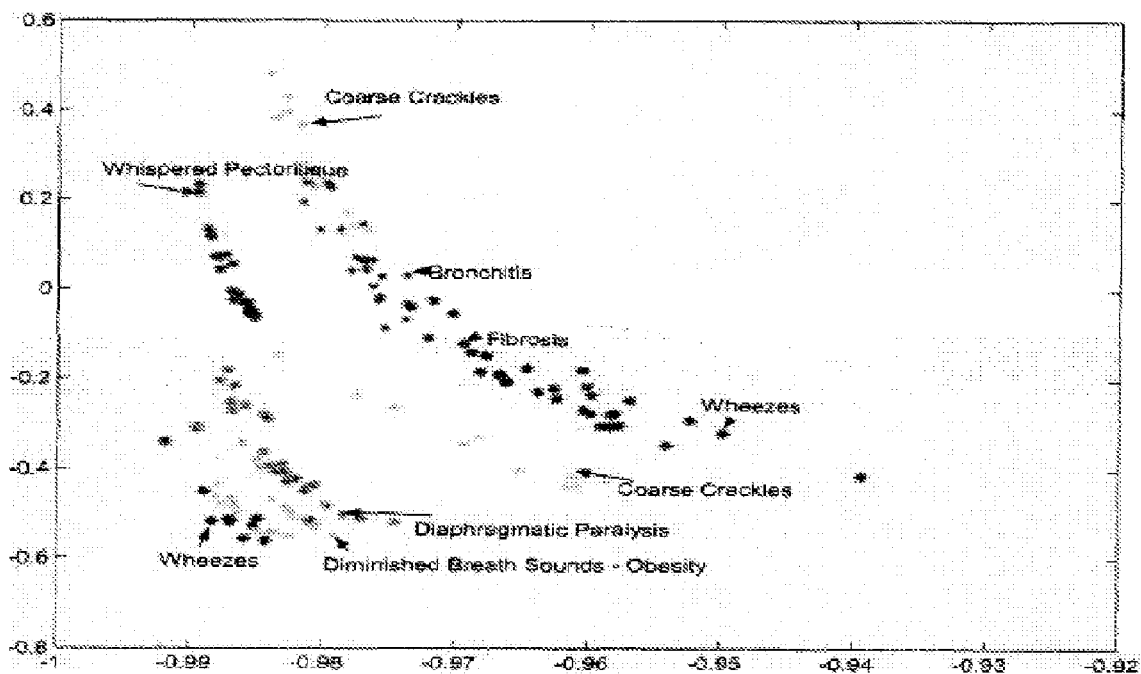
FIG. 7 is a two-dimensional (2-D) representation of various diseases using PARCOR coefficients 3 and 4.

FIGS. 2, 3, 4 and 5 show the location of data points for particular diseases, when the second and third LPC and PARCOR coefficients are used as X-Y coordinates in a two dimensional plane. FIG. 6 shows the location of data points for particular diseases when PARCOR coefficients 2 and 3 are used, and FIG. 7 shows the location of data points for the same diseases when the third and fourth PARCOR coefficients are used as X-Y coordinates in 2-D. These data points are recorded for the inhalation (inspiration) cycle.

Each dot or star on these diagrams represents data collected from a patient with a particular disease. It appears in FIG. 6 that there is some overlap of the clusters in these two dimensional representations. Actually this overlap does not occur in reality, because in reality multiple features are used which are represented in multiple dimensions, and not just in two. If two clusters overlap for instance like in FIG. 6 (set PARCOR 2 and 3) for Wheezes and Fibrosis, one can represent the same samples in other two dimensions like in FIG. 7 (set PARCOR 3 and 4) where the same data sample points for Wheezes and Fibrosis are well separated and do not overlap. Similarly, to separate clusters one could use (the set PARCOR 4 and 5), (the set PARCOR 5 and 6), (the set PARCOR 3 and LPC 3) etc.

Referencing again to FIGS. 6 and 7, and to further explain this use of the LPC and PARCOR coefficients according to the present invention for recognition of diseases, MATLAB extracted from the precessed lung sound recordings, 20 LPC (LPC1, LPC2, etc.) and 20 PARCOR coefficients (PARCOR1, PARCOR2, etc.). To represent these 20 coefficients graphically for data points associated with various diseases, a 20 dimensional space is needed. When representing data on paper on an X-Y diagram we use only two dimensions. It is possible that in the 20 dimensional space clusters of some diseases, overlap in some two dimensional planes appear and these diseases cannot be recognized and separated. See, for example, FIG. 6 where the clusters for Wheezes and Fibrosis are not well separated when PARCOR 2 and PARCOR 3 are used. However if we look at this 20 dimensional cluster from another projection, for example, using PARCOR 3 and PARCOR 4 as in FIG. 7, the clusters for Wheezes and Fibrosis are well separated.

Explaining further, one notices some overlap of the clusters in these two dimensional representations. Actually this overlap does not occur in reality, because in reality we use multiple features which are represented in multiple dimensions, and not just in two. If two clusters overlap for instance like in FIG. 6 (set PARCOR 2 and 3) for Wheezes and Fibrosis, we can represent the same samples in other two dimensions like in FIG. 7 (set PARCOR 3 and 4) where the same data sample points for Wheezes and Fibrosis do not overlap. Similarly, we could use (the set PARCOR 4 and 5), (the set PARCOR 5 and 6), (the set PARCOR 3 and LPC 3) etc. as noted above.

Since each of the features is multidimensional, the number of combinations is extremely large, and if we combine the components of multidimensional vectors in two dimensional sets, there is an extremely high probability that there are projections in which clusters will not overlap. In other words, the possibility of mis-diagnosis when two clusters overlap can be eliminated if additional features and/or dimensions are used. Consequently, adding additional features helps clusters to separate better, without overlapping.

It is noted that if the Neural Net of the present invention is used for classification as will be explained later in this disclosure, the overlap of clusters in some dimensions is not important, because the neural net takes simultaneously all dimensions into consideration.

As noted, the features are extracted from the lung signal using the MATLAB "Signal Processing Package," and the two dimensional diagrams are plotted using the MATLAB functions cbr2d and cfb2d.

Thus the simple Graphical Classifier (GC) can be used to select the best features to identify a particular lung disease. These best features are the dominant features for that disease. The best features and the best dimensions are the ones that separate the clusters best. However, if the clusters do not overlap, it is not necessary to project the data points into other dimensions. The simple classifier is therefore adequate for the diagnosis of lung diseases, or it can be used for dominant feature selection as well.

Summarizing the Graphical Approach

1. Bring the samples of lung sounds, e.g. stored on a CD, into the computer.

2. Extract the LPC and PARCOR coefficients from these signals using MATLAB and the prepackaged software routines from the MATLAB Signal Processing Package.

3. Generate and plot two dimensional diagrams for LPC and PARCOR coefficients using the MATLAB cbr2d and cfb2d routines, which should look similar to FIG. 2 to 7 of this disclosure.

4. Plot these diagrams for the second and third LPC and PARCOR coefficients.

5. If clusters for some diseases overlap, use the third and fourth coefficients instead, or other two coefficients so that there is no overlap.

Artificial Neural Networks

Artificial neural networks (ANN) are very useful classifiers and also computational tools because of their ability to model and solve complex problems. ANNs emulate functions of the human brain. ANNs can be trained to perform a particular functions which is a valuable characteristic because an ANN can be trained and not programmed.

ANNs have become a very popular since they can be used in many scientific applications, like in computer science, information theory, and signal-image processing. Due to the various applications, many different ANN models and implementations have come into view. Most of the ANNs are direct descendants of Rosenblant's perception circuits (1958) (Looney, G. C., "Pattern recognition using neural networks", Oxford University Press, 1997).

The n-dimensional input vector applied to the input of a perceptron generates a weighted sum of the input vectors, next a threshold value θ is subtracted from this sum. The generated output passes through a non-linear function x, and the result is obtained at the output of the perceptron.

The Neural Network (NN) Approach Classifier

The advantage of the NN classifier is that it makes decisions based on all selected dominant features simultaneously. Many classifiers can be used for this application, however the NN classifier proved to be suitable for this application.

It will be understood, however, that other suitable classifiers can be used as well. It is important to note that samples used in training and testing the Neural Net are real sounds from lungs recorded from real patients, and not artificially generated sounds.

The application of the Neural Net will be illustrated on data collected from patients who have Fibrosis and Bronchitis.

After extracting features (LPC and PARCOR coefficients) for each of these diseases, the Neural Network is used as a classifier. The implemented Neural Network is the network specified by Mathworks and documented in the MATLAB manual. This neural network was chosen because it is easy to set up, because it is relatively fast and because it can solve non-linear classification problems.

The preliminary step is training of the Neural Network, so that the trained network can be used for the classification of signals. The function used for training is the MATLAB function "nn_xxx_yy", where 'xxx' denotes the used feature, and 'yy' denotes the disease. The use of combined features is not necessary, because obtained results are good even if just one set of features is used at a time. If only one set of features is used at a time, the training time is minimized. In addition, this leads to a simpler neural network.

A detailed description of the nn_xxx_yy function can be found In the MATLAB manual.

The Implemented Neural Network—Example

In the presented example samples of signals for two particular diseases have been divided into a training set, and a testing set. Two sets of features, the LPC coefficients and the PARCOR coefficients have been extracted. The two sets are approximately of the same size, with the testing set a little larger. The Neural Net is trained with data from the training set and then tested with data from the testing set. The training set contains objects of two classes, diseased and healthy, with a ratio of approximately 1 to 4. This decision was made assuming that the probability that a sample belongs to a particular disease is smaller than the probability that it does not. The number of training and testing data samples for the two diseases presented in this example are listed in Tables 1 and 2.

TABLE 1

Number of data samples used for training and testing NN for Bronchitis

| Samples | Training set | Testing Set |
| --- | --- | --- |
| Bronchitis | 12 | 10 |
| Non-Bronchitis | 40 | 72 |

TABLE 2

Number of data samples for training and testing NN for Fibrosis

| Samples | Training set | Testing Set |
| --- | --- | --- |
| Fibrosis | 12 | 10 |
| Non-Fibrosis | 40 | 72 |

The ratio of 4 to 1 is also reflected in the distribution of the objects in each class in the training procedure. The number of neurons in the network is selected by trial and error. The number of iterations is another parameter that was defined. The learning process should run until no further improvements can be detected, otherwise overtraining may occur. Overtraining worsens the performance of the network and its ability for prediction. In the described example the trial and error method was used in order to determine the optimal number of iterations. A series of experiments had been performed to determine the optimal number of neurons and iterations. The performance of each set (neurons, iterations) was determined by two factors. The most important one is the percentage of correctly classified samples that belong to a particular disease. The second factor is the percentage of correctly classified samples that do not belong to the particular disease. A common way to present results of this type is the confusion matrix.

TABLE 3

Example of the implemented Confusion Matrix

| | | |
| --- | --- | --- |
| Samples from ill persons | A | B |
| Samples from healthy persons | C | D |

A: The number of samples from ill persons that are classified as ill.
B: The number of samples from ill persons that are classified as healthy.
C: The number of samples from healthy persons that are classified as ill
D: The number of samples from healthy persons that are classified as healthy.

Table 4 shows the final number for neurons and iterations that were used in the test.

TABLE 4

Number for neurons and iterations that were used in the test

| | Neurons | Iterations |
| --- | --- | --- |
| Bronchitis LPC coefficients | 50 | 3000 |
| Fibrosis LPC coefficients | 80 | 3000 |
| Bronchitis PARCOR coefficients | 50 | 2500 |
| Fibrosis PARCOR coefficients | 50 | 2500 |

Results

To verify the accuracy of the method, after the parameters and the configuration of the neural network were determined, the analysis with the Neural Network was performed several times for each disease. The following tables summarize the classification results.

TABLE 5

Confusion Matrix - Bronchitis using LPC coefficients

| Bronchitis | 100% | 0% |
|---|---|---|
| Non Bronchitis | 2% | 98% |

TABLE 6

Confusion Matrix - Bronchitis using PARCOR coefficients

| Bronchitis | 100% | 0% |
|---|---|---|
| Non Bronchitis | 0% | 100% |

TABLE 7

Confusion Matrix - Fibrosis using LPC coefficients

| Fibrosis | 100% | 0% |
|---|---|---|
| Non Fibrosis | 15% | 85% |

TABLE 8

Confusion Matrix - Fibrosis using PARCOR coefficients

| Fibrosis | 100% | 0% |
|---|---|---|
| Non Fibrosis | 6% | 94% |

Summarizing the Neural Network Approach

1. Bring the samples of Lung Sounds from the chest into the computer.
2. Extract the LPC and PARCOR Coefficients from these signals using MATLAB, and the prepackaged software routines from the MATLAB Signal Processing Package.
3. Use the GA classifier of the Graphical Approach to select the best features (the GA classifier).
4. Construct the Neural Net using the prepackaged MATLAB routines—follow guidelines from the MATLAB manual.
5. Train the Neural Net to recognize particular diseases using the extracted LPC and PARCOR coefficients for these diseases. Use the best features.
6. The output of the Neural Net will indicate if the lungs are healthy, and identify the disease if the lungs are diseased.
7. The NN method will give good results even if step 3 above is left out, however if step 3 is implemented the accuracy will be higher.

The inventor has found that better classification results were accomplished when PARCOR, partial correlation coefficients were used, although classification results are very good with LPC coefficients as well. The implementation of both sets of features, LPC and PARCOR provide good results, however other sets of features can be used to practice the present invention.

Data Acquisition and Processing Details

Breathing sounds that were used for the present invention were obtained from the lung sound database issued by a reputable clinic. These sounds are professionally recorded with large signal-to-noise ratios. Since the inspiratory segment of the respiratory cycle is most important, the expiratory phase was ignored. 134 inspiratory phases with durations between 0.5 and 0.8 seconds were used. Among these samples were 22 samples associated with chronic bronchitis and 22 samples associated with interstitial fibrosis. 54 samples were associated with several diseases like lobar pneumonia. The remaining 36 samples were inspiratory phases obtained from healthy persons.

Breath sounds are in the form of sequential respiratory cycles, therefore it is necessary to isolate only one cycle. Moreover if characteristic sounds for diseases under investigation appear in the inspiratory cycle, the inspiratory cycle should be separated from the respiratory cycle. For example this is the case for chronic bronchitis, and interstitial fibrosis. If signals are obtained from a data base these two phases can be separated using a wave editor, and if signals are obtained from a live patient, the patient can be asked to inhale and hold.

After the acquisition of the needed signals in the inspiratory phase, the signals were converted into a suitable form for processing. At this point MATLAB undertakes most of the work. MATLAB calls the function sig_process. This function is used for preparation of the signals for further processing. Next MATLAB calls three other functions, downsample, convrt, obtain_c. The syntax of the function is sig_process('xx', n), where 'xx' is the first two letters of the investigating disease and n is the number of the signals.

The downsample function does what its name implies; downsample the signals from 44.1 kHz to 16 kHz. It reads the wave files under the directory/research/signals, performs the downsampling operation and stores the resulting signals under the directory/research/16k_signals. The original frequency of the data is 44.1 kHz, the data is contained in a CD-ROM in digital form. This high frequency of 44.1 kHz produces a large number of samples. In addition, the number of required coefficients to represent these sounds accurately is proportional to the sampling frequency. A large number of samples and a large number of coefficients increase the computation cost. Therefore a lower sampling frequency is a very good step to reduce the time and required memory for computations. The reason for choosing 16 kHz as the downsampling frequency is because the human ear is not sensitive to signals whose frequencies are higher than 16 kHz so that the downsampling frequency does not interfere with auscultation.

The next function is called by sig_process is the convrt function. This function converts the wave (*.wav) files into MATLAB binary files (*.mat). The advantages of the specific procedure is the minimization of the disk space required for storage and the reduced time needed for MATLAB to load binary files, instead of wave files.

This function loads the signals under the directory/research/16k_signals and stores the binary files under the directory/research/16k_signals_bin. The generated files are temporary and are altered after processing with the consequently function.

The next used function is the obtain_c function. The purpose of this function is the extraction of the feature coefficients and of the and storage of these coefficients in binary files. The obtain_c function loads the binary files under the directory/research/16k_signals_bin, evaluates the features and then saves them under the directory/research/16k_coeff, with the same file name. At the present time, each of the new generated file contains two matrices that include feature coefficients, the first matrix contains the linear prediction coefficients, while the second matrix contains partial correlation coefficients. The calculation of the features executed by the functions lpcauto and atorc which were developed by Jeffrey Sorensen (http://www.campbellsorensen.com/soreni/) under the terms of GNU General Public License.

The default parameter for the number of coefficients that is evaluated for each feature is twenty. This is not an arbitrary number, but it is based on the theory of specific features that were used. The theory states that the complete representation of a signal using the LPC coefficients is strongly dependent by the sampling frequency. We use one coefficient for every kHz and four supplementary coefficients for the zeros. For that reason a 16 kHz signal results in the evaluation of twenty coefficients.

This preliminary procedure is needed before feature extraction. At this point the features are stored in MATLAB binary files and they are ready for use by the neural network.

More on the Linear Prediction and Autoregressive Method

If a biomedical process is an autoregressive method, the autoregressive parameters can be estimated on the basis of the linear prediction method. The prediction power error $e^2[n]$ is the excitation input power and the prediction coefficients are the autoregressive parameters. The transfer function of the autoregressive process is given by $A(z)=1-z^{-1}H(z)$ or is given by $A(z)=1-a_1z^{-1}-a_2z^{-2}+ \ldots +a_nz^{-n}$, where $H[x]$ represents the Wiener filter and M represents the autoregressive filter order. In the z-domain we can written $E(z)=A(z)Y(z)$.

The autoregressive model is also referred to as the "all-pole model" because it is represented by a function with poles and no zeros.

The Autocorrelation Method:

One way of calculating the prediction coefficients of the autoregressive process is the autocorrelation method. The method exploits the estimated autocorrelation lags in the Yule-Walker and is explained in Makhoul, J., "Linear prediction: a tutorial review", Proc. IEEE 63:561-580, 1975. The autocorrelation lags are found as a function of an autoregressive model order and a higher order autocorrelation function (ACF). The ACF parameters can be calculated as a function of the data sequence and the variance of the noise power can be estimated using the Yule-Walker equation. Using the ACF an autocorrelation matrix can be created containing the Toeplitz autocorrelation matrix with dimensions (M+1)×(M+1), a prediction vector and a noise power vector. The prediction coefficients are obtained using the Levinson recursion and the prediction coefficients at stage M can be obtained recursively from those previously calculated at stage M−1 (see: Kay, S. M., "Recursive maximum likelihood estimation of autoregressive processes", IEEE Trans. Accoust. Speech Signal Processing ASSP-28:292-303, 1980). The relationship between the new prediction-error filter and the old one can be calculated (Orfanidis, S., "Optimum Signal Processing", MacMillan, New York, 1985) as $A_{M+1}(z)=A_m(z)-g_{m+1}z^{-m-1}A_m(z^{-1})$, where g are the reflection (PARCOR) coefficients at stage m. The reflection coefficients at m-th stage can also be calculated.

A summary of the autocorrelation method using the Levinson recursion can be found at Akay, M., "Biomedical Signal Processing", Academic Press Limited, 1994.

Order Selection of the Autoregression Model

There are several approaches proposed for selecting the order of the filter. The number of the coefficients of the filter is equal with its order and the goal is the minimization of the prediction error. The order can be calculated using the Akaine final prediction criterion discussed in: Akaine, H., "Statistical predictor identification", Ann. Inst. Statist. Math. 22:203-217, 1970 where $E_M$ is the estimation of the mean-squared error, M is the order of the filter and N is the number of the samples of the input data.

The number of the coefficients can also be estimated with the Akaine information criterion, which minimizes the information entropy of the signal (Akaine, H., "A new look at the statistical model identification", IEEE Trans. Autom. Control AC19:726-723, 1974).

Rissanen (Rissasen, J., "Modeling by shortest data description", Automatica 14:465-471, 1978) proposed another method, in which the filter order can be estimated.

Resolution of the Autoregressive Analysis

The resolution of the autoregressive analysis can also be calculated according to Akay, M., "Biomedical Signal Processing", Academic Press Limited, 1994, as a function of sampling interval, the order of the filter and the signal-to-noise ratio. Qualitatively, the resolution is defined as the extent to which the frequencies corresponding to two closely located peaks can be distinguished.

General Considerations

The present invention is not concerned with providing a diagnosis or for treating a patient, but rather concerns technical solutions to technical problems that may assist a physician in reaching a diagnosis for or treatment of a patient.

The invention is not limited to the disclosed embodiments. Also, the word "comprising" does not here exclude other elements or steps, and use of the words "a" or "an" does not exclude a plurality. Further, a single processor or other unit may fulfill the functions of several elements recited in the claims, and features recited in separate dependent claims may be advantageously combined. Reference signs in the claims or elsewhere in this disclosure should not be construed as limiting the scope of the claims.

While specific embodiments of the invention have been shown and described in detail to illustrate the application of the principles of the invention, it will be understood that the invention may be embodied otherwise without departing from such principles.

What is claimed is:

1. A method of identifying a lung disease that produces sounds that are characteristic of the lung disease, comprising subjecting the sounds to autoregressive modeling to recognize and thus identify the lung disease and projecting at least one two-dimensional representation of autocorrelation coefficients of the autoregressive modeling for the sounds and identifying the disease by selecting at least one pair of coefficients that separate clusters of samples in the representation to identify the lung disease.

2. A method according to claim 1, wherein the use of autoregressive modeling includes identifying autocorrelation coefficients for the sounds to recognize the lung disease.

3. A method according to claim 2, including using at least one of LPC and PARCOR coefficients as the autocorrelation coefficients.

4. A method according to claim 1, wherein the coefficients are at least one of LPC and PARCOR coefficients.

5. A method according to claim 1, using discriminant analysis to select dominant features of the autoregressive modeling and using neural network analysis of the for dominant features for identifying the disease.

6. A method according to claim 1, including storing in a computer, a data base of dominant features from pre-recorded sounds from lungs with at least one lung disease during a training phase, obtaining sounds from lungs of a subject to be tested, conditioning the sounds to create a signal that can be subjected to analysis in the computer, using the autoregressive modeling on the signal in the computer and using the data base with autoregressively modeled signal to identify the disease.

7. A method of identifying a lung disease that produces sounds that are characteristic of the lung disease, comprising subjecting the sounds to autoregressive modeling to recognize and thus identify the lung disease and projecting a plurality of two-dimensional representations of autocorrelation coefficients of the autoregressive modeling for the sounds, selected features of the representations that provide relatively good correlation to the lung disease as compared to feature that give relatively poor correlation to the lung disease, and identifying the disease by selection of at least one pair of coefficients that separate clusters of samples in the representation for the features that provide relatively good correlation to the lung disease.

8. A method of identifying a lung disease that produces sounds that are characteristic of the lung disease, comprising subjecting the sounds to autoregressive modeling to recognize and thus identify the lung disease and projecting at least one two-dimensional representation of autocorrelation coefficients of the autoregressive modeling for the sounds, subjecting the representation to discriminant analysis to select dominant features of the representation and using neural network analysis of the dominant features for identifying the disease.

9. A method of identifying a lung disease that produces sounds that are characteristic of the lung disease, comprising subjecting the sounds to autoregressive modeling to recognize and thus identify the lung disease and wherein the use of autoregressive modeling includes extracting a plurality of autocorrelation coefficients from the sounds, subjecting at least some of the coefficients to multi-dimensional projection to extract features of the projection, and using the features to identifying the lung disease.

10. An apparatus for identifying a lung disease in a subject, the lung disease producing lung sounds that are characteristic of the lung disease, the apparatus comprising: a stethoscope for acquiring the lung sounds from the subject; a transducer operatively connected to the stethoscope for converting the lung sounds to a signal; and a computer-based analyzer for analyzing the signal to identify the lung disease and wherein the computer-based analyzer comprises a computer that is programmed with a program for analyzing the signal to identify the lung disease using autoregressive modeling and wherein the program plots at least one two dimensional representation of autocorrelation coefficients of the autoregressive modeling for the signal and identifies the disease by selection at least one pair of coefficients that separate clusters of samples in the representation.

11. An apparatus according to claim 10, wherein the stethoscope includes at least 31 one hose for conveying the sounds, and the transducer comprises a microphone connected to the hose for picking up sounds in the hose.

12. An apparatus according to claim 10, wherein the computer-based analyzer comprises a computer that is programmed for analyzing the signal to identify the lung disease using autoregressive modeling.

13. An apparatus according to claim 1, wherein the program identifies autocorrelation coefficients of the autoregressive modeling for the signal to identify the lung disease.

14. An apparatus according to claim 13, wherein the program uses at least one of LPC and PARCOR coefficients as the autocorrelation coefficients.

15. An apparatus according to claim 10, wherein the coefficients are at least one of LPC and PARCOR coefficients.

16. An apparatus for identifying a lung disease in a subject, the lung disease producing lung sounds that are characteristic of the lung disease, the apparatus comprising: a stethoscope for acquiring the lung sounds from the subject; a transducer operatively connected to the stethoscope for converting the lung sounds to a signal; and a computer-based analyzer for analyzing the signal to identify the lung disease and wherein the computer-based analyzer comprises a computer that is programmed with a program for analyzing the signal to identify the lung disease using autoregressive modeling, wherein the program plots a plurality of two-dimensional representations of autocorrelation coefficients of the autoregressive modeling for the sounds, and selects features of the representations that provide relatively good correlation to the lung disease as compared to feature that give relatively poor correlation to the lung disease, and identifies the disease by selection at least one pair of coefficients that separate clusters of samples in the representation for the features that provide relatively good correlation to the lung disease.

17. An apparatus for identifying a lung disease in a subject, the lung disease producing lung sounds that are characteristic of the lung disease, the apparatus comprising: a stethoscope for acquiring the lung sounds from the subject; a transducer operatively connected to the stethoscope for converting the lung sounds to a signal; and a computer-based analyzer for analyzing the signal to identify the lung disease and wherein the computer-based analyzer comprises a computer that is programmed with a program for analyzing the signal to identify the lung disease using autoregressive modeling, wherein the program plots at least one two-dimensional representation of autocorrelation coefficients of the autoregressive modeling for the sounds, and subjects the representation to discriminant analysis to select dominant features of the representation, and uses neural network analysis of the dominant features for identifying the disease.

18. An apparatus according to claim 17, wherein the program uses discriminant analysis to select dominant features of the autoregressive modeling and using neural network analysis of the for dominant features for identifying the disease.

19. An apparatus according to claim 17, a data base stored in the computer-based analyzer, of dominant features from pre-recorded sounds from lungs with at least one lung disease during a training phase, means for conditioning the sounds to create the signal that can be subjected to analysis in the analyzer, the analyzer being programed to perform autoregressive modeling on the signal and to use the data base with autoregressively modeled signal to identify the disease.

20. An apparatus for identifying a lung disease in a subject, the lung disease producing lung sounds that are characteristic of the lung disease, the apparatus comprising: a stethoscope for acquiring the lung sounds from the subject; a transducer operatively connected to the stethoscope for converting the lung sounds to a signal; and a computer-based analyzer for analyzing the signal to identify the lung disease, wherein the program extracts a plurality of autocorrelation coefficients from the sounds, subjects at least some of the coefficients to multi-dimensional projection to extract features of the projection, and uses the features to identifying the lung disease.

21. An apparatus for identifying a disease in a subject, the disease producing sounds that are characteristic of the disease, the apparatus comprising: means for acquiring the sounds; and a computer-based analyzer for analyzing the sounds to identify the disease using autoregressive modeling, wherein the program projects at least one two-dimensional representation of autocorrelation coefficients of the autoregressive modeling for the sound and identifies the disease by selection of at least one pair of coefficients that separate clusters of samples in the representation.

22. An apparatus according to claim 21, wherein the computer-based analyzer comprises a computer that is programmed with a program for analyzing the sounds to identify the disease using autoregressive modeling, the program using at least one of LPC and PARCOR coefficients as autocorrelation coefficients for the modeling.

23. An apparatus according to claim 21, wherein the coefficients are at least one of LPC and PARCOR coefficients.

24. An apparatus according to claim 21, wherein the program uses discriminant analysis to select dominant features of the autoregressive modeling and using neural network analysis of the for dominant features for identifying the disease.

25. An apparatus according to claim 21, including a data base stored in the computer-based analyzer, of dominant features from pre-recorded sounds from lungs with at least one lung disease during a training phase, means for conditioning the sounds to create the signal that can be subjected to analysis in the analyzer, the analyzer being programed to perform autoregressive modeling on the signal and to use the data base with autoregressively modeled signal to identify the disease.

26. An apparatus for identifying a disease in a subject, the disease producing sounds that are characteristic of the disease, the apparatus comprising: means for acquiring the sounds; and a computer-based analyzer for analyzing the sounds to identify the disease using autoregressive modeling, wherein the program plots a plurality of two-dimensional representations of autocorrelation coefficients of the autoregressive modeling for the sounds, and selects features of the representations that provide relatively good correlation to the lung disease as compared to feature that give relatively poor correlation to the lung disease, and identifies the disease by selection of at least one pair of coefficients that separate clusters of samples in the representation for the features that provide relatively good correlation to the disease.

27. An apparatus for identifying a disease in a subject, the disease producing sounds that are characteristic of the disease, the apparatus comprising: means for acquiring the sounds; and a computer-based analyzer for analyzing the sounds to identify the disease using autoregressive modeling, wherein the program plots at least one two-dimensional representation of autocorrelation coefficients of the autoregressive modeling for the sounds, and subjects the representation to discriminant analysis to select dominant features of the representation, and uses neural network analysis of the dominant features for identifying the disease.

28. An apparatus for identifying a disease in a subject, the disease producing sounds that are characteristic of the disease, the apparatus comprising: means for acquiring the sounds; and a computer-based analyzer for analyzing the sounds to identify the disease using autoregressive modeling, wherein the program extracts a plurality of autocorrelation coefficients from the sounds, subjects at least some of the coefficients to multi-dimensional projection to extract features of the projection, and uses the features to identifying the disease.

* * * * *